(12) United States Patent     (10) Patent No.: US 8,027,821 B2
Maranas et al.     (45) Date of Patent: Sep. 27, 2011

(54) METHOD FOR DETERMINING GENE KNOCKOUTS

(75) Inventors: Costas D. Maranas, Port Matilda, PA (US); Anthony R. Burgard, State College, PA (US); Priti Pharkya, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 453 days.

(21) Appl. No.: 10/616,659

(22) Filed: Jul. 9, 2003

(65) Prior Publication Data

US 2004/0009466 A1    Jan. 15, 2004

Related U.S. Application Data

(60) Provisional application No. 60/444,933, filed on Feb. 3, 2003, provisional application No. 60/417,511, filed on Oct. 9, 2002, provisional application No. 60/395,763, filed on Jul. 10, 2002.

(51) Int. Cl.
*G06G 7/48*    (2006.01)
(52) U.S. Cl. .......................................................... 703/11
(58) Field of Classification Search .................... 702/20; 435/4, 6
See application file for complete search history.

(56) References Cited

U.S. PATENT DOCUMENTS

| | | | |
|---|---|---|---|
| 4,520,103 | A | 5/1985 | Ensley, Jr. |
| 6,117,108 | A | 9/2000 | Woehr et al. |
| 2002/0012939 | A1 | 1/2002 | Palsson |
| 2002/0142321 | A1 | 10/2002 | Palsson et al. |
| 2002/0168654 | A1 | 11/2002 | Maranas et al. |
| 2003/0073092 | A1 | 4/2003 | Maranas et al. |
| 2005/0079482 | A1* | 4/2005 | Maranas et al. .................. 435/4 |

FOREIGN PATENT DOCUMENTS

| | | |
|---|---|---|
| JP | 2000-268018 | 3/1999 |
| WO | WO 98/18814 | 5/1998 |
| WO | WO 00/18906 | 4/2000 |
| WO | WO 00/42559 | 7/2000 |
| WO | WO 01/90346 | 11/2001 |
| WO | WO 02/055995 A2 | 7/2002 |
| WO | WO 2004/018621 | 4/2004 |

OTHER PUBLICATIONS

Voit, Optimization in Integrated Biochemical Systems, Biotechnology and Bioengineering, 1992, 40: 572-582.*
Yang et al., Metabolic Flux Analysis of *Escherichia coli* Deficient in the Acetate Production Pathway and Expressing the *Bacillus subtilis* Acetolactate Synthase, Metabolic Engineering, 1999, 1:26-34.*
Schilling et al, Combining Pathway Analysis with Flux Balance Analysis for the Comprehensive Study of Metabolic Systems, Biotechnology and Bioengineering, 71(4):286-306, 2001.*
Klamt et al.,FluxAnalyzer: exploring structure, pathways, and flux distributions in metabolic networks on interactive flux maps, Bioinformatics, 19(2):261-269, 2003.*
Papin et al., Metabolic pathways in the post-genome era, May 2003, Trends in Biochemical Sciences, 28(5):250-258.*
Bhaska et al. (Reviews in Chemical Engineering, vol. 16, Issue 1, p. 1-54, 2000).*
Anandalingam et al. (Annals of Operations Research, vol. 34, p. 1-11, 1992).*
Burgard, A. P. et al., Minimal Reaction Sets for *Escherichia coli* Metabolism under Different Growth Requirements and Uptake Environments. Biotechnology Progress., 17(5):791-797 (2001).
Burgard, A.P. et al., Probing the Performance Limits of the *Escherichia coil* Metabolic Network Subject to Gene Additions or Deletions. Biotechnology and Bioengineering, 74(5):364-375 (2001).
Biebl, H, Menzel, K, Zeng, AP, Deckwer, WD. 1999. "Microbial production of 1,3- propanediol". Appl Environ Microbiol 52: 289-297.
Burgard, AP, Maranas, CD. 2001. "Probing the performance limits of the *Escherichia coli* metabolic network subject to gene additions or deletions". Biotechnol Bioeng 74: 364-375.
Burgard, AP, Maranas, CD. 2003. Optimization-based framework for inferring and testing hypothesized metabolic objective functions. Biotechnol Bioeng 82(6): 670-7.
Burgard, AP, Vaidyaraman, S, Maranas, CD. 2001. "Minimal Reaction Sets for *Escherichia coli* Metabolism under Different Growth Requirements and Uptake Environments." Biotechnol Prog 17: 791-797.
Cameron, DC, Altaras, ND, Hoffman, ML, Shaw, AJ. 1998. "Metabolic engineering of propanediol pathways." Biotechnol Prog 14(1): 116-25.
Compagno, C, Boschi, F, Ranzi, BM. 1996. "Glycerol production in a triose phosphate isomerase deficient mutant of *Saccharomyces cerevisiae*". Biotechnol Prog 12(5): 591-5.
Edwards, JS, Ibarra, RU, Palsson, Bo. 2001. "In silico predictions of *Escherichia coli* metabolic capabilities are consistent with experimental data". Nat Biotechnol 19(2): 125-30.
Edwards, JS, Palsson, BO. 2000. "The *Escherichia coli* MG1655 in silico metabolic genotype: its definition, characteristics, and capabilities". Proc Natl Acad Sci U S A 97(10): 5528-33.

(Continued)

*Primary Examiner* — Karlheinz R Skowronek

(74) *Attorney, Agent, or Firm* — McKee, Voorhees & Sease, P.L.C.

(57) ABSTRACT

A method for determining candidates for gene deletions and additions using a model of a metabolic network associated with an organism, the model includes a plurality of metabolic reactions defining metabolite relationships, the method includes selecting a bioengineering objective for the organism, selecting at least one cellular objective, forming an optimization problem that couples the at least one cellular objective with the bioengineering objective, and solving the optimization problem to yield at least one candidate.

22 Claims, 6 Drawing Sheets

OTHER PUBLICATIONS

Gupta, S, Clark, DP. 1989. "*Escherichia coli* derivatives lacking both alcohol dehydrogenase and phosphotransacetylase grow anaerobically by lactate fermentation." J Bacteriol 171(7): 3650-5.

Hartlep, M, Hussmann, W, Prayitno, N, Meynial-Salles, I, Zeng, AP. 2002. "Study of two-stage processes for the microbial production of 1,3-propanediol from glucose". Appl Microbiol Biotechnol 60(1-2): 60-6.

Ibarra, RU, Edwards, JS, Palsson, BO. 2002. "*Escherichia coli* K-12 undergoes adaptive evolution to achieve in silico predicted optimal growth". Nature 420(6912): 186-9.

Menendez, C, Bauer, Z, Huber, H, Gad'on, N, Stetter, KO, Fuchs, G. 1999. "Presence of acetyl coenzyme a (CoA) carboxylase and propionyl-CoA carboxylase in autotrophic Crenarchaeota and indication for operation of a 3-hydroxypropionate cycle in autotrophic carbon fixation". J Bacteriol 181(4): 1088-98.

Segre, D, Vitkup, D, Church, GM. 2002. "Analysis of optimality in natural and perturbed metabolic networks". Proc Natl Acad Sci U S A 99(23): 15112-7.

Stols, L, Donnelly, MI. 1997. "Production of succinic acid through overexpression of NAD(+)-dependent malic enzyme in an *Escherichia coli* mutant". Appl Environ Microbiol 63(7): 2695-701.

Zeikus, JG, Jain, MK, Elankovan, P. 1999. "Biotechnology of succinate acid production and markets for derived industrial products". Appl Microbiol Biotechnol 51: 545-552.

Zeng, AP, Biebl, H. 2002. Bulk chemicals from biotechnology: the case of 1,3- propanediol production and the new trends. Adv Biochem Eng Biotechnol 74: 239-59.

Zhu, MM, Lawman, PD, Cameron, DC. 2002. "Improving 1,3-propanediol production from glycerol in a metabolically engineered *Escherichia coli* by reducing accumulation of sn-glycerol-3-phosphate". Biotechnol Prog >18(4): 694-9.

Arigoni, et al., "A genome-based approach for the identification of essential bacterial genes," Nat. Biotechnol. 16 (9):851-856 (1998).

Aristidou et al., "Modification of central metabolic pathway in *Escherichia coli* to reduce acetate accumulation by heterolgous expression of the *Bacillus subtilis* acetolactate synthase gene," Biotechnol. Bioeng. 44:944-951 (1994).

Arita, "Metabolic construction using shortest paths," Sim. Pract. Theory, 8(1-2):109-125 (2000).

Arita, "The metabolic world of *Escherichia coli* is not small," Proc. Natl. Acad. Sci. USA 101(6):1543-1547 (2004).

Bailey et al., "Combining evidence using p-values: application to sequence homology searches," Bioinformatics 14 (1):48-54 (1998).

Blattner, et al., "The complete genome sequence of *Escherichia coli* K-12," Science 277(5331):1453-74 (1997).

Bogarad et al., "A hierarchical approach to protein molecular evolution," Proc. Natl. Acad. Sci. USA 96(6):2591-2595 (1999).

Bond et al., "Electricity production by *Geobacter sulfurreducens* attached to electrodes," Appl. Environ. Microbiol. 69 (3):1548-1555 (2003).

Burgard et al., "Optknock: a bilevel programming framework for identifying gene knockout strategies for microbial strain optimization," Biotechnol. Bioeng. 84(6):647-657 (2003).

Castellanos et al., "A modular minimal cell model: purine and pyrimidine transport and metabolism," Proc. Natl. Acad. Sci. USA 101(17):6681-6686 (2004).

Causey et al., "Engineering *Escherichia coli* for efficient conversion of glucose to pyruvate," Proc. Natl. Acad. Sci. USA 101(8):2235-2240 (2004).

Chen et al., "Computer Program for Calculating the Melting Temperature of Degenerate Oligonucleotides Used in PCR or Hybridization," BioTechniques, 22:1158-1160 (1997).

Chistoserdova et al., "Multiple formate dehydrogenase enzymes in the facultative methylotroph *Methylobacterium extorquens* AM1 are dispensable for growth on methanol," J. Bacteriol. 186:22-28 (2004).

Cho et al., "Ethical considerations in synthesizing a minimal genome," Science 286:2087-2090 (1999).

Covert et al., "Metabolic modeling of microbial strains in silico," Trends Biochem. Sci. 26:179-186 (2001).

Das et al., International Journal of Hydrogen Energy, 26:13-28 (2001).

David et al., "Reconstruction of the central carbon metabolism of *Aspergillus niger*," Eur J. Biochem. 270 (21):4243-4253 (2003).

Delgado et al., "Identifying Rate-Controlling Enzymes in Metabolic Pathways without Kinetic Parameters," Biotechnol. Prog. 7:15-20 (1991).

Demain, "Stunning achievements of industrial microbiology," ASM News 65:311-316 (1999).

Edwards et al., "How will bioinformatics influence metabolic engineering?," Biotechnol. Bioeng. 58(2-3):162-169 (1998).

Edwards et al., "Metabolic flux balance analysis and the in silico analysis of *Escherichia coli* K-12 gene deletions," BMC Bioinformatics 1(1):1-10 (2000).

Ellis et al., "The University of Minnesota Biocatalysis/Biodegradation Database: post-genomic data mining," Nucl. Acids. Res. 31(1):262-265 (2003).

Eppstein, "Finding the k Shortest Paths" in 35th IEEE Symp Foundations of Comp Sci, Santa Fe, pp. 154-165 (1994).

Fisher "The langragean relaxation method for solving integer programming," Manage. Sci. 27:1 (1981).

Geoffrion "Lagrangean relaxation and its uses in integer programming," Mat. Program. Stud. 2:82 (1974).

Henriksen et al., "Growth energetics and metabolic fluxes in continuous cultures of *Penicillium chrysogenum*," J. • Biotechnol. 45:149-164 (1996).

Hugler et al., "Malonyl-coenzyme a reductase from *Chioroflexus aurantiacus*, a key enzyme of the 3-hydroxypropionate cycle for autotrophic CO(2) fixation," J. Bacteriol. 184(9):2404-2410 (2002).

Hutchinson et al., "Global transposon mutagenesis and a minimal *Mycoplasma genome*," Science 286 (5447):2165-2169 (1999).

Itaya, "An estimation of minimal genome size required for life," FEBS Lett. 362(3):257-260 (1995).

Jorgensen, et al., "Metabolic flux distributions in *Penicillium chrysogenum* during fed-batch cultivations," Biotechnol. Bioeng. 46(2):117-131 (1995).

Kanehisa and Goto, "KEGG: kyoto encyclopedia of genes and genomes," Nucl. Acids Res. 28(1):27-30 (2000).

Kanehisa et al., "The KEGG resource for deciphering the genome," Nucl. Acids Res. 32(Database issue):D277-80 (2004).

Karp et al., "Eco Cyc: Encyclopedia of *Escherichia coli* genes and metabolism," Nuc. Acids Res. 27(1):55-58 (1999).

Karp et al., "The EcoCyc and MetaCyc databases," Nucl. Acids Res. 28(1):56-59 (2000).

Karp et al., "The EcoCyc Database," Nucl. Acids Res. 30(1):56-58 (2002).

Kataoka et al., "Studies of hydrogen production by continuous culture system of hydrogen-producing anaerobic bacteria," Wat. Sci. Tech. 36:41-47 (1997).

Kauffman et al., "Advances in flux balance analysis," Curr. Opin. Biology. London, GB, 14(5):491-496 (2003).

Keasling et al., "Engineering Polyphosphate Metabolism in *Escherichia coli*: Implications for Bioremediation of Inorganic Contaminants," Biotechnol. Bioeng. 58(2-3):321-239 (1998).

Korotkova et al., "Poly-beta-hydroxybutyrate biosynthesis in the facultative methylotroph *Methylobacterium extorquens* AM1: identification and mutation of gap11, gap20, and phaR," J. Bacteriol. 184(22):6174-6181 (2002).

Krieger et al., "MetaCyc: a multiorganism database of metabolic pathways and enzymes," Nucl. Acids Res. 32 (Database issue), D438-D4342 (2004).

Lovley, "Cleaning up with genomics: applying molecular biology to bioremediation", Nat. Rev. Microbiol. 1(1):35-44 (2003).

Lutz et al., "Creating multiple-crossover DNA libraries independent of sequence identity," Proc. Natl. Acad. Sci. USA 98 (20):11248-11253 (2001).

Mavrovouniotis, et al., "Synthesis of Biochemical Production Routes," Comp. Chem. Engineer. 16:605-619 (1992).

Mavrovouniotis et al., "Computer-aided synthesis of biochemical pathways," Biotechnol. Bioeng. 36 (11):1119-1132 (1990).

McShan et al., "PathMiner: predicting metabolic pathways by heuristic search," Bioinformatics. 19(13):1692-1698 (2003).

Methe et al., "Genome of *Geobacter sulfurreducens*: metal reduction in subsurface environments," Science 302 (5652):1967-9 (2003).

Misawa et al., "Production of beta-carotene in *Zymomonas mobilis* and *Agrobacterium tumefaciens* by introduction of the biosynthesis genes from *Erwinia uredovora*," Appl. Environ. Microbiol. 57(6):1847-1849 (1991).

Moore et al., "Modeling DNA Mutation and Recombination for Directed Evolution Experiments" J. Theor. Biol. 205 (3):483-503 (2000).

Moore et al., "Predicting crossover generation in DNA shuffling," Proc. Natl. Acad. Sci. USA 98(6):3226-3231 (2001).

Mushegian et al., "A minimal gene set for cellular life derived by comparison of complete bacterial genomes," Proc. Natl. Acad. Sci. USA 93(19):10268-10273 (1996).

Nakamura and Whited, "Metabolic engineering for the microbial production of 1,3-propanediol," Curr. Opin. Biotechnol. 14(5):454-459 (2003).

Oh et al., "Gene expression profiling by DNA microarrays and metabolic fluxes in *Escherichia coli*," Biotechnol. Prog. 16(2):278-286 (2000).

Overbeek et al., "WIT: integrated system for high-throughput genome sequence analysis and metabolic reconstruction," Nucl. Acids. Res. 28(1):123-125 (2000).

Palsson, "The Challenges of in Silico Biology," Nat. Biotechnol. 18(11):1147-1150 (2000).

Papoutsakis et al., "Equations and Calculations of Product Yields and Preferred Pathways for Butanediol and Mixed-Acid Fermentations", Biotechnology and Bioengineering 17:50-66 (1985).

Papoutsakis, "Equations and calculations for fermentations of butyric acid bacteria," Biotechnol. Bioeng. 26(2):174-187 (1984).

Pennisi, "Laboratory Workhorse Decoded," Science 277:1432-1434 (1997).

Pharkya et al., "Exploring the overproduction of amino acids using the bilevel optimization framework OptKnock," Biotechnol. Bioeng. 84(7):887-899 (2003).

Pharkya, et al., "OptStrain: A computational framework for redesign of microbial production systems", Genome Res. 14:2367-2376 (2004).

Pramanik et al., "Stoichiometric Model of *Escherichia coli* Metabolism: Incorporation of Growth-Rate Dependent Biomass Composition and Mechanistic Energy Requirements," Biotechnol. Bioeng. 56(4):398-421 (1997).

Quackenbush et al., "The TIGR Gene Indices: analysis of gene transcript sequences in highly sampled eukaryotic species," Nucleic Acids Res. 29:159-165 (2001).

Reed et al., "An expanded genome-scale model of *Escherichia coli* K-12 (iJR904 GSM/GPR," Genome Biol. 4(9):R54 (2003).

Richmond et al., "Genome-wide expression profiling in *Escherichia coli* K-12," Nucl. Acids Res. 27(19):3821-3835 (1999).

SantaLucia Jr., "A unified view of polymer, dumbbell, and oligonucleotide DNA nearest-neighbor thermodynamics," Proc. Natl. Acad. Sci. USA, 95(4):1460-1465 (1998).

Savageau, "Biochemical Systems Analysis," J. Theor. Biol. 25:365-369 (1969).

Schilling et al., "The Underlying Pathway Structure of Biochemical Reaction Networks," Proc. Natl. Acad. Sci. USA, 95 (8):4193-4198 (1998).

Schilling et al., "Toward metabolic phenomics: analysis of genomic data using flux balances," Biotechnol Prog, 15:288-295 (1999).

Segre et al., "From annotated genomes to metabolic flux models and kinetic parameter fitting," Omics, 7(3):301-316 (2003).

Selkov, et al., "MPW: the Metabolic Pathways Database," Nucl Acids Res, 26(1):43-45 (1998).

Sun, "Modeling DNA Shuffling," Ann. Conf. Res. Comp. Mol. Biol. Proc. Second. Ann. Intl Conf. Comp. Mol. Biol. p. 251-257 (1998).

Supplemental European Search Report, The Penn State Research Foundation, EP 0478 2168 Dated Jul. 8, 2009.

Tomita, et al., "E-Cell: software environment for whole-cell simulation," Bioinformatics 15(1):72-84 (1999).

Tomita, "The E-Cell Project: Towards Integrative Simulation of cellular Processes," New Gen. Comput. 18:1-12 (2000).

Valdes et al., "Metabolic reconstruction of sulfur assimilation in the extremophile *Acidithiobacillus ferrooxidans* based on genome analysis," BMC Genomics 4:51 (2003).

Vallino et al., "Metabolic flux distributions in *Corynebacterium glutamicium* during growth and lysine overproduction," Biotechnol. Bioeng. 41:633-646 (1993).

Varma et al., "Metabolic Capabilities of *Escherichia coli*: I. Synthesis of Biosynthetic Precursors and Cofactors", J. theor. Biol. 165:477-502 (1993).

Varma et al., "Stoichiometric flux balance models quantitatively predict growth and metabolic by-product secretion in wild-type *Escherichia coli* W3110," Appl. Environ. Microbiol. 60(10):3724-3731 (Oct. 1994).

Varner et al., "Mathematical Models of Metabolic Pathways," Curr. Opin. Biotechnol. 10(2):146-150 (Apr. 1999).

Wang et al., "Cadimum removel by a new strain *Pseudomonas aeruginosa* in aerobic culture," App. Environ. Microbial. 63:4075-4078 (1997).

Xie et al., "Energy metabolism and ATP balance in animal cell cultivation using a stoichiometrically based reaction network," Biotechnol. Bioeng. 52(5):591-601 (1996).

Xie et al., "Integrated approaches to the design of media and feeding strategies for fed-batch cultures of animal cells," Trends Biotechnol. 15(3):109-113 (1997).

Xie et al., "Material Balance Studies on Animal Cell Metabolism Using Stoichiometrically Based Reaction Network," Biotechnol. Bioeng. 52:579-590 (1996).

Xie et al., "Stoichiometric analysis of animal cell growth and its application in medium design," Biotechnol. Bioeng. 43 (11):1164-1174 (1994).

URL. www.che.udel.edu/edwardsgroup/LAB/NBT_ExpPhPP/FBAPrimer/FBAC "Appendix 1: Flux balance analysis primer," (As printed Jan. 4, 2002).

GAMS User Guide, Brooke et al., GAMS Development Corp, 1998, p. 1-276, URL http://www.ilog.com/products/cplex/) accessed via the GAMS (Brooke, et al., (1998).

Supplementary European Search Report (co-pending EP 03 79 2962) dated Apr. 11, 2007.

Hatzimanikatis, Vassily et al., "Analysis and design of metabolic reaction networks via mixed-integer linear optimization", A1ChE Journal, 42(5):1277-1292 (1996).

Varma, Amit et al., "Biochemical production capabilities of *Escherichia coli*", Biotechnology and Bioengineering, 42:59-73 (1993).

Torres, Nestor V., et al., "An Indirect Optimization Method for Biochemical Systems: Description of Method and Application to the Maximization of the Rate of Ethanol, Glycerol, and Carbohydrate Production in *Saccharomyces cerevisiae*", Biotechnology and Bioengineering, 55(5):758-772 (1997).

Covert, M.W., et al., "Regulation of Gene Expression in Flux Balance Models of Metabolism", J. of Theoretical Biology, 213:73-88 (2001).

\* cited by examiner maximize bioengineering objective
  (through gene knockouts)
subject to maximize cellular objective
    (over fluxes)
  subject to ○ fixed substrate uptake
    ○ network stoichiometry
    ○ blocked reactions identified
      by outer problem
  number of knockouts ≤ limit

METHOD FOR DETERMINING GENE KNOCKOUTS

GRANT REFERENCE

This invention was made with government support under Grant No. DE-FG03-01ER25499. awarded by the Department of Energy and under Grant No. BES0120277, awarded by the National Science Foundation. The Government has certain rights in the invention.

CROSS-REFERENCE TO RELATED APPLICATIONS

This application is based on U.S. Patent Application Ser. No. 60/395,763, filed Jul. 10, 2002; U.S. Patent Application Ser. No. 60/417,511, filed October, 9, 2002, and U.S. Patent Application Ser. No. 60/444,933, filed Feb. 3, 2003, each of which is herein incorporated by reference in its entirety.

BACKGROUND OF THE INVENTION

The systematic development of engineered microbial strains for optimizing the production of chemicals or biochemicals is an overarching challenge in biotechnology (Stephanopoulos et al., 1998). However, in the absence of metabolic and genetic engineering interventions, the product yields of many microorganisms are often far below their theoretical maximums. This is expected because cellular metabolism is primed, through natural selection, for the maximum responsiveness to the history of selective pressures rather than for the overproduction of specific chemical compounds. Not surprisingly, the behavior of metabolic networks is governed by internal cellular objectives which are often in direct competition with chemical overproduction targets.

The recent explosion of annotated sequence information along with a wealth of chemical literature has enabled the reconstruction of genome-scale metabolic networks for many microorganisms (Edwards and Palsson, 2000; Schilling and Palsson, 2000; Schilling et al., 2002; Forster et al., 2003). This information, used in the context of the flux balance analysis (FBA) modeling framework (Varma and Palsson, 1993), has been employed extensively to explore the integrated functions of metabolic networks (Burgard and Maranas, 2001; Burgard et al., 2001; Papin et al., 2003; Price et al., 2003). FBA models typically invoke the optimization of a particular cellular objective (e.g., ATP production (Majewski and Domach, 1990; Ramakrishna et al., 2001), biomass formation (Varma and Palsson, 1993,1994), minimization of metabolic adjustment (Segre et al., 2002)), subject to network stoichiometry, to suggest a likely flux distribution. Stoichiometric models of *Escherichia coli* (*E. coli*) metabolism utilizing the biomass maximization hypothesis have been in some cases successful at (i) predicting the lethality of gene knockouts (Edwards and Palsson, 2000; Badarinarayana et al., 2001), (ii) identifying the correct sequence of byproduct secretion under increasingly anaerobic conditions (Varma et al., 1993), and (iii) quantitatively predicting cellular growth rates under certain conditions (Edwards et al., 2001). Interestingly, recent work suggests that even when FBA predictions under the biomass maximization assumption seem to fail, metabolic networks can be evolved, for certain cases, towards maximum growth (i.e., biomass yield) through adaptive evolution (Ibarra et al., 2002).

The ability to investigate the metabolism of single-cellular organisms at a genomic scale, and thus systemic level, motivates the need for novel computational methods aimed at identifying strain engineering strategies.

Thus, one object, feature, or advantage of the present invention is to provide a method for computationally suggesting the manner in which to achieve bioengineering objectives.

A further object, feature or advantage of the present invention is to determine candidates for gene deletion or addition through use of a model of a metabolic network.

A still further object, feature or advantage of the present invention is to provide an optimized method for computationally achieving a bioengineering objective.

Yet another object, feature or advantage of the present invention is to provide an optimized method for computationally achieving a bioengineering objective that is robust.

One or more of these and/or other objects, features and advantages of the present invention will become apparent after review of the following detailed description of the disclosed embodiments and the appended claims.

BRIEF SUMMARY OF THE INVENTION

The systematic development of engineered microbial strains for optimizing the production of chemical or biochemicals is an overarching challenge in biotechnology. The advent of genome-scale models of metabolism has laid the foundation for the development of computational procedures for suggesting genetic manipulations that lead to overproduction. The present invention describes a computational framework for suggesting gene deletion strategies leading to the overproduction of chemicals or biochemicals in *E. coli*. This is accomplished by ensuring that a drain towards growth resources (i.e., carbon, redox potential, and energy) is accompanied, due to stoichiometry, by the production of a desired production. Specifically, the computation framework identifies multiple gene deletion combinations that maximally couple a postulated cellular objective (e.g., biomass formation) with externally imposed chemical production targets. This nested structure gives rise to a bilevel optimization problems which are solved based on a transformation inspired by duality theory. This procedure of this framework, by coupling biomass formation with chemical production, suggest a growth selection/adaption system for indirectly evolving overproducing mutants.

One embodiment of the invention is directed to a method for determining candidates for gene deletions and additions. The method uses a model of a metabolic network associated with an organism. The model includes a number of metabolic reactions defining metabolite relationships. The method includes selecting a bioengineering objective for the selecting the organism. Next, at least one cellular objective is selected. An optimization problem is formed that couples the cellular objective with the bioengineering objective. Finally, the optimization problem is solved to yield at least one candidate.

BRIEF DESCRIPTION OF THE DRAWINGS

FIG. 1 depicts the bilevel optimization structure of Optknock. The inner problem performs the flux allocation based on the optimization of a particular cellular objective (e.g., maximization of biomass yield, MOMA). The outer problem then maximizes the bioengineering objective (e.g., chemical production) by restricting access to key reactions available to the optimization of the inner problem.

DETAILED DESCRIPTION OF THE PREFERRED EMBODIMENT

Figure 2:
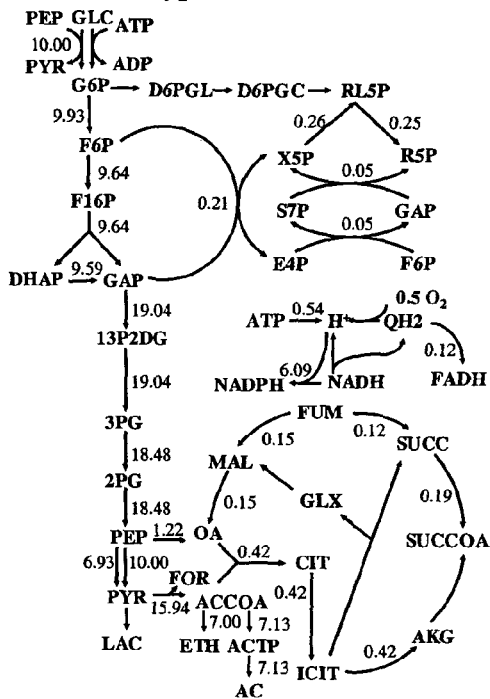
FIG. 2 depicts the flux distributions of the (A) wild-type *E. coli*, (B) succinate mutant B, (C) succinate mutant C, and (D) lactate mutant C networks that maximize biomass yield under anaerobic conditions.
Figure 2:
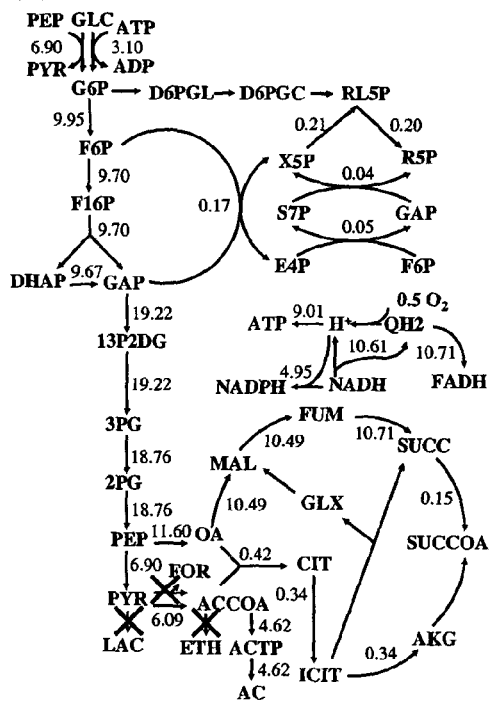
Figure 2:
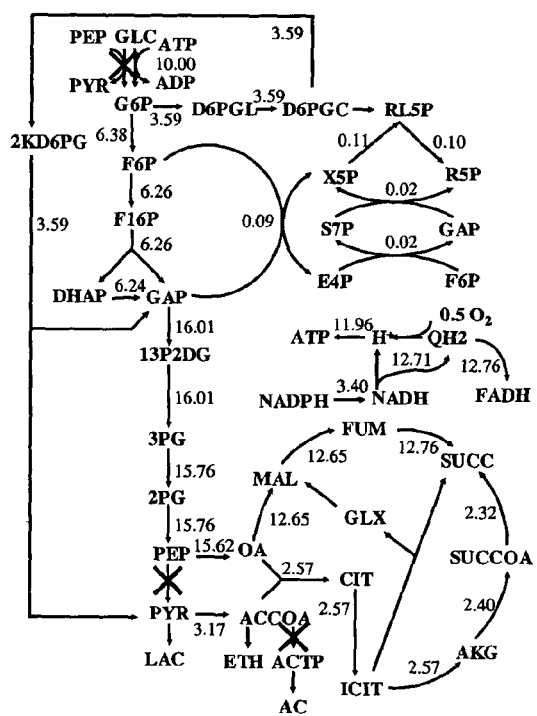
Figure 2:
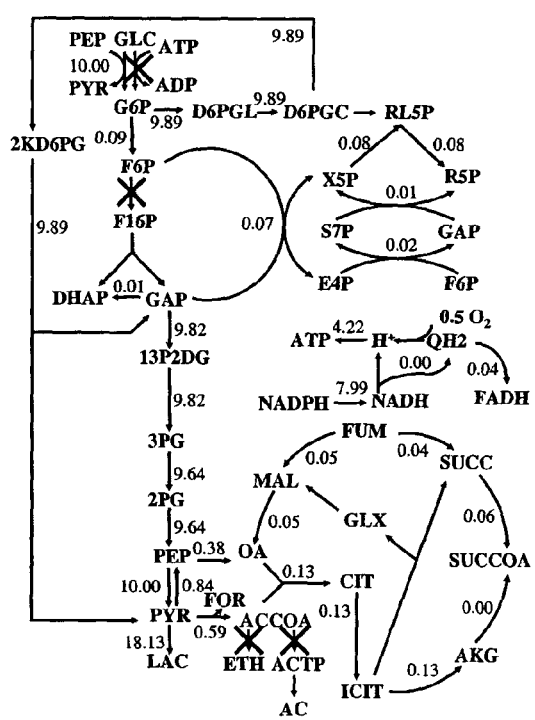

The ability to investigate the metabolism of single-cellular organisms at a genomic scale, and thus systemic level, motivates the need for novel computational methods aimed at identifying strain engineering strategies. The present invention includes a computational framework termed OptKnock for suggesting gene deletion strategies leading to the overproduction of specific chemical compounds in *E. coli*. This is accomplished by ensuring that the production of the desired chemical becomes an obligatory byproduct of growth by "shaping" the connectivity of the metabolic network. In other words, OptKnock identifies and subsequently removes metabolic reactions that are capable of uncoupling cellular growth from chemical production. The computational procedure is designed to identify not just straightforward but also non-intuitive knockout strategies by simultaneously considering the entire *E. coli* metabolic network as abstracted in the in silico *E. coli* model of Palsson and coworkers (Edwards and Palsson, 2000). The complexity and built-in redundancy of this network (e.g., the *E. coli* model encompasses 720 reactions) necessitates a systematic and efficient search approach to combat the combinatorial explosion of candidate gene knockout strategies.

The nested optimization framework shown in FIG. 1 is developed to identify multiple gene deletion combinations that maximally couple cellular growth objectives with externally imposed chemical production targets. This multi-layered optimization structure involving two competing optimal strategists (i.e., cellular objective and chemical production) is referred to as a bilevel optimization problem (Bard, 1998). Problem formulation specifics along with an elegant solution procedure drawing upon linear programming (LP) duality theory are described in the Methods section. The OptKnock procedure is applied to succinate, lactate, and 1,3-propanediol (PDO) production in *E. coli* with the maximization of the biomass yield for a fixed amount of uptaken glucose employed as the cellular objective. The obtained results are also contrasted against using the minimization of metabolic adjustment (MOMA) (Segre et al., 2002) as the cellular objective. Based on the OptKnock framework, it is possible identify the most promising gene knockout strategies and their corresponding allowable envelopes of chemical versus biomass production in the context of succinate, lactate, and PDO production in *E. coli*.

A preferred embodiment of this invention describes a computational framework, termed OptKnock, for suggesting gene deletions strategies that could lead to chemical production in *E. coli* by ensuring that the drain towards metabolites/compounds necessary for growth resources (i.e., carbons, redox potential, and energy) must be accompanied, due to stoichiometry, by the production of the desired chemical. Therefore, the production of the desired product becomes an obligatory byproduct of cellular growth. Specifically, OptKnock pinpoints which reactions to remove from a metabolic network, which can be realized by deleting the gene(s) associated with the identified functionality. The procedure was demonstrated based on succinate, lactate, and PDO production in *E. coli* K-12. The obtained results exhibit good agreement with strains published in the literature. While some of the suggested gene deletions are quite straightforward, as they essentially prune reaction pathways competing with the desired one, many others are at first quite non-intuitive reflecting the complexity and built-in redundancy of the metabolic network of *E. coli*. For the succinate case, OptKnock correctly suggested anaerobic fermentation and the removal of the phosphotranferase glucose uptake mechanism as a consequence of the competition between the cellular and chemical production objectives, and not as a direct input to the problem. In the lactate study, the glucokinase-based glucose uptake mechanism was shown to decouple lactate and biomass production for certain knockout strategies. For the PDO case, results show that the Entner-Doudoroff pathway is more advantageous than EMP glycolysis despite the fact that it is substantially less energetically efficient. In addition, the so far popular tpi knockout was clearly shown to reduce the maximum yields of PDO while a complex network of 15 reactions was shown to be theoretically possible of "leaking" flux from the PPP pathway to the TCA cycle and thus decoupling PDO production from biomass formation. The obtained results also appeared to be quite robust with respect to the choice for the cellular objective.

The present invention contemplates any number of cellular objectives, including but not limited to maximizing a growth rate, maximizing ATP production, minimizing metabolic adjustment, minimizing nutrient uptake, minimizing redox production, minimizing a Euclidean norm, and combinations of these and other cellular objectives.

It is important to note that the suggested gene deletion strategies must be interpreted carefully. For example, in many cases the deletion of a gene in one branch of a branched pathway is equivalent with the significant up-regulation in the other. In addition, inspection of the flux changes before and after the gene deletions provides insight as to which genes need to be up or down-regulated. Lastly, the problem of mapping the set of identified reactions targeted for removal to its corresponding gene counterpart is not always uniquely specified. Therefore, careful identification of the most economical gene set accounting for isozymes and multifunctional enzymes needs to be made.

Preferably, in the OptKnock framework, the substrate uptake flux (i.e., glucose) is assumed to be 10 mmol/gDW·hr.

Therefore, all reported chemical production and biomass formation values are based upon this postulated and not predicted uptake scenario. Thus, it is quite possible that the suggested deletion mutants may involve substantially lower uptake efficiencies. However, because OptKnock essentially suggests mutants with coupled growth and chemical production, one could envision a growth selection system that will successively evolve mutants with improved uptake efficiencies and thus enhanced desired chemical production characteristics.

Where there is a lack of any regulatory or kinetic information within the purely stoichiometric representation of the inner optimization problem that performs flux allocation, OptKnock is used to identify any gene deletions as the sole mechanism for chemical overproduction. Clearly, the lack of any regulatory or kinetic information in the model is a simplification that may in some cases suggest unrealistic flux distributions. The incorporation of regulatory information will not only enhance the quality of the suggested gene deletions by more appropriately resolving flux allocation, but also allow us to suggest regulatory modifications along with gene deletions as mechanisms for strain improvement. The use of alternate modeling approaches (e.g., cybernetic (Kompala et al., 1984; Ramakrishna et al., 1996; Varner and Ramkrishna, 1999), metabolic control analysis (Kacser and Burns, 1973; Heinrich and Rapoport, 1974; Hatzimanikatis et al., 1998)), if available, can be incorporated within the OptKnock framework to more accurately estimate the metabolic flux distributions of gene-deleted metabolic networks. Nevertheless, even without such regulatory or kinetic information, OptKnock provides useful suggestions for strain improvement and more importantly establishes a systematic framework. The present invention naturally contemplates future improvements in metabolic and regulatory modeling frameworks.

Methods

The maximization of a cellular objective quantified as an aggregate reaction flux for a steady state metabolic network comprising a set $\mathcal{N}=\{1, \ldots, N\}$ of metabolites and a set $\mathcal{M}=\{1, \ldots, M\}$ of metabolic reactions fueled by a glucose substrate is expressed mathematically as follows, $$\text{maximize } v_{cellular\ objective} \text{ (Primal)}$$

$$\text{subject to } \sum_{j=1}^{M} S_{ij} v_j = 0, \forall\ i \in \mathcal{N}$$

$$v_{pts} + v_{glk} = v_{glc\_uptake}\ mmol/gDW \cdot hr$$

$$v_{atp} \geq v_{atp\_main}\ mmol/gDW \cdot hr$$

$$v_{biomass} \geq v_{biomass}^{target}\ 1/hr$$

$$v_j \geq 0, \forall\ j \in \mathcal{M}_{irrev}$$

$$v_j \leq 0, \forall\ j \in \mathcal{M}_{secr\_only}$$

$$v_j \in \mathcal{R}, \forall\ j \in \mathcal{M}_{rev}$$

where $S_{ij}$ is the stoichiometric coefficient of metabolite i in reaction j, $v_j$ represents the flux of reaction j, $v_{glc\_uptake}$ is the basis glucose uptake scenario, $v_{atp\_main}$ is the non-growth associated ATP maintenance requirement, and $v_{biomass}^{target}$ is a minimum level of biomass production. The vector v includes both internal and transport reactions. The forward (i.e., positive) direction of transport fluxes corresponds to the uptake of a particular metabolite, whereas the reverse (i.e., negative) direction corresponds to metabolite secretion. The uptake of glucose through the phosphotransferase system and glucokinase are denoted by $v_{pts}$ and $v_{glk}$, respectively. Transport fluxes for metabolites that can only be secreted from the network are members of $\mathcal{M}_{secr\_only}$. Note also that the complete set of reactions $\mathcal{M}$ is subdivided into reversible $\mathcal{M}_{rev}$ and irreversible $\mathcal{M}_{irrev}$ reactions. The cellular objective is often assumed to be a drain of biosynthetic precursors in the ratios required for biomass formation (Neidhardt and Curtiss, 1996). The fluxes are reported per 1 gDW·hr such that biomass formation is expressed as g biomass produced/gDW·hr or 1/hr.

The modeling of gene deletions, and thus reaction elimination, first requires the incorporation of binary variables into the flux balance analysis framework (Burgard and Maranas, 2001; Burgard et al., 2001). These binary variables, $$y_j = \begin{cases} 1 \text{ if reaction flux } v_j \text{ is active} \\ 0 \text{ if reaction flux } v_j \text{ is not active} \end{cases}, \forall\ j \in \mathcal{M}$$

assume a value of one if reaction j is active and a value of zero if it is inactive. The following constraint, $$v_j^{min} \cdot y_j \leq v_j \leq v_j^{max} \cdot y_j, \forall j \in \mathcal{M}$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. In this study, $v_j^{min}$ and $v_j^{max}$ are identified by minimizing and subsequently maximizing every reaction flux subject to the constraints from the Primal problem.

The identification of optimal gene/reaction knockouts requires the solution of a bilevel optimization problem that chooses the set of reactions that can be accessed ($y_j=1$) so as the optimization of the cellular objective indirectly leads to the overproduction of the chemical or biochemical of interest (see also FIG. 1). Using biomass formation as the cellular objective, this is expressed mathematically as the following bilevel mixed-integer optimization problem $$\text{maximize } v_{chemical}\ (OptKnock)$$
$$y_j$$

$$\text{subject to} \begin{pmatrix} \text{maximize } v_{biomass} & \text{(Primal)} \\ v_j & \\ \text{subject to} \quad \sum_{j=1}^{M} S_{ij} v_j = 0, \quad \forall\ i \in \mathcal{N} \\ v_{pts} + v_{glk} = v_{glc\_uptake} \\ v_{atp} \geq v_{atp\_main} \\ v_{biomass} \geq v_{biomass}^{target} \end{pmatrix}$$

$$v_j^{min} \cdot y_j \leq v_j \leq v_j^{max} \cdot y_j, \forall\ \in \mathcal{M}$$

$$y_j = \{0, 1\}, \forall\ \in \mathcal{M}$$

$$\sum_{j \in M} (1 - y_j) \leq K$$

where K is the number of allowable knockouts. The final constraint ensures that the resulting network meets a minimum biomass yield, $v_{biomass}^{target}$.

The direct solution of this two-stage optimization problem is intractable given the high dimensionality of the flux space (i.e., over 700 reactions) and the presence of two nested optimization problems. To remedy this, we develop an efficient solution approach borrowing from LP duality theory which shows that for every linear programming problem (primal) there exists a unique optimization problem (dual) whose optimal objective value is equal to that of the primal problem. A similar strategy was employed by (Burgard and Maranas, 2003) for identifying/testing metabolic objective functions from metabolic flux data. The dual problem (Ignizio and Cavalier, 1994) associated with the OptKnock inner problem is $$\text{minimize } v_{atp\_main} \cdot \mu_{atp} + v_{biomass}^{target} \cdot \mu_{biomass} + v_{glc\_uptake} \cdot glc \quad \text{(Dual)}$$

$$\text{subject to } \sum_{i=1}^{N} \lambda_i^{stoich} S_{i,glk} + \mu_{glk} + glc = 0$$

$$\sum_{i=1}^{N} \lambda_i^{stoich} S_{i,pts} + \mu_{pts} + glc = 0$$

$$\sum_{i=1}^{N} \lambda_i^{stoich} S_{i,biomass} + \mu_{biomass} = 1$$

$$\sum_{i=1}^{N} \lambda_i^{stoich} S_{ij} + \mu_j = 0, \; \forall \; j \in \mathcal{M}, \; j \neq glk, \, pts, \, biomass$$

$$\mu_j^{min} \cdot (1 - y_j) \leq \mu_j \leq \mu_j^{max} \cdot (1 - y_j), \; \forall \; j \in \mathcal{M}_{rev} \text{ and } j \notin \mathcal{M}_{secr\_only}$$

$$\mu_j \geq \mu_j^{min} \cdot (1 - y_j), \; \forall \; j \in \mathcal{M}_{rev} \text{ and } \mathcal{M}_{secr\_only}$$

$$\mu_j \leq \mu_j^{max} \cdot (1 - y_j), \; \forall \; j \in \mathcal{M}_{irrev} \text{ and } j \notin \mathcal{M}_{secr\_only}$$

$$\mu_j \in \mathcal{R}, \; \forall \; j \in \mathcal{M}_{irrev} \text{ and } \mathcal{M}_{secr\_only}$$

$$\lambda_i^{stoich} \in \mathcal{R}, \; \forall \; j \in \mathcal{N}$$

$$glc \in \mathcal{R}$$

where $\lambda_i^{stoich}$ is the dual variable associated with the stoichiometric constraints, glc is the dual variable associated with the glucose uptake constraint, and $\mu_j$ is the dual variable associated with any other restrictions on its corresponding flux $v_j$ in the Primal. Note that the dual variable $\mu_j$ acquires unrestricted sign if its corresponding flux in the OptKnock inner problem is set to zero by enforcing $y_j=0$. The parameters $\mu_j^{min}$ and $\mu_j^{max}$ are identified by minimizing and subsequently maximizing their values subject to the constraints of the Dual problem.

If the optimal solutions to the Primal and Dual problems are bounded, their objective function values must be equal to one another at optimality. This means that every optimal solution to both problems can be characterized by setting their objectives equal to one another and accumulating their respective constraints. Thus the bilevel formulation for OptKnock shown previously can be transformed into the following single-level MILP $$\text{maximize } v_{chemical} \quad (OptKnock)$$

$$\text{subject to}$$

$$v_{biomass} = v_{atp\_main} \cdot \mu_{atp} + v_{biomass}^{target} \cdot \mu_{biomass} + v_{glc\_uptake} \cdot glc$$

$$\sum_{j=1}^{M} S_{ij} v_j = 0, \; \forall \; i \in \mathcal{N}$$

$$v_{pts} + v_{glk} = v_{glc\_uptake} \quad mmol/gDW \cdot hr$$

$$v_{atp} \geq v_{atp\_main} \quad mmol/gDW \cdot hr$$

$$\sum_{i=1}^{N} \lambda_i^{stoich} S_{i,glk} + \mu_{glk} + glc = 0$$

-continued $$\sum_{i=1}^{N} \lambda_i^{stoich} S_{i,pts} + \mu_{pts} + glc = 0$$

$$\sum_{i=1}^{N} \lambda_i^{stoich} S_{i,biomass} + \mu_{biomass} = 1$$

$$\sum_{i=1}^{N} \lambda_i^{stoich} S_{ij} + \mu_j = 0, \; \forall \; j \in \mathcal{M}, \; j \neq glk, \, pts, \, biomass$$

$$\sum_{j \in M} (1 - y_j) \leq K$$

$$v_{biomass} \geq v_{biomass}^{target}$$

$$\mu_j^{min} \cdot (1 - y_j) \leq \mu_j \leq \mu_j^{max} \cdot (1 - y_j), \; \forall \; j \in \mathcal{M}_{rev} \text{ and } j \notin \mathcal{M}_{secr\_only}$$

$$\mu_j \geq \mu_j^{min} \cdot (1 - y_j), \; \forall \; j \in \mathcal{M}_{rev} \text{ and } \mathcal{M}_{secr\_only}$$

$$\mu_j \leq \mu_j^{max} \cdot (1 - y_j), \; \forall \; j \in \mathcal{M}_{irrev} \text{ and } j \notin \mathcal{M}_{secr\_only}$$

$$\mu_j \in \mathcal{R}, \; \forall \; j \in \mathcal{M}_{irrev} \text{ and } \mathcal{M}_{secr\_only}$$

$$v_j^{min} \cdot y_j \leq v_j \leq v_j^{max} \cdot y_j, \; \forall \; j \in \mathcal{M}$$

$$\lambda_i^{stoich} \in \mathcal{R}, \; \forall \; j \in \mathcal{N}$$

$$glc \in \mathcal{R}$$

$$y_j = \{0, 1\}, \; \forall \; j \in \mathcal{M}$$

An important feature of the above formulation is that if the problem is feasible, the optimal solution will always be found. In this invention, the candidates for gene knockouts included, but are not limited to, all reactions of glycolysis, the TCA cycle, the pentose phosphate pathway, respiration, and all anaplerotic reactions. This is accomplished by limiting the number of reactions included in the summation (i.e., $$\left(\text{i.e., } \sum_{j \in Central\,Metabolism} (1 - y_j) = K\right).$$

Problems containing as many as 100 binary variables were solved in the order of minutes to hours using CPLEX 7.0 accessed via the GAMS modeling environment on an IBM RS6000-270 workstation. It should be understood, however, that the present invention is not dependent upon any particular type of computer or environment being used. Any type can be used to allow for inputting and outputting the information associated with the methodology of the present invention. Moreover, the steps of the methods of the present invention can be implemented in any number of types software applications, or languages, and the present invention is not limited in this respect.

It will be appreciated that other embodiments and uses will be apparent to those skilled in the art and that the invention is not limited to these specific illustrative examples.

Example 1

Succinate and Lactate Production

Which reactions, if any, that could be removed from the *E. coli* K-12 stoichiometric model (Edwards and Palsson, 2000) so as the remaining network produces succinate or lactate whenever biomass maximization is a good descriptor of flux allocation were identified. A prespecified amount of glucose (10 mmol/gDW·hr), along with unconstrained uptake routes for inorganic phosphate, oxygen, sulfate, and ammonia are provided to fuel the metabolic network. The optimization step could opt for or against the phosphotransferase system, glucokinase, or both mechanisms for the uptake of glucose. Secretion routes for acetate, carbon dioxide, ethanol, formate, lactate and succinate are also enabled. Note that because the glucose uptake rate is fixed, the biomass and product yields are essentially equivalent to the rates of biomass and product production, respectively. In all cases, the OptKnock procedure eliminated the oxygen uptake reaction pointing at anaerobic growth conditions consistent with current succinate (Zeikus et al., 1999) and lactate (Datta et al., 1995) fermentative production strategies.

Figure 3:
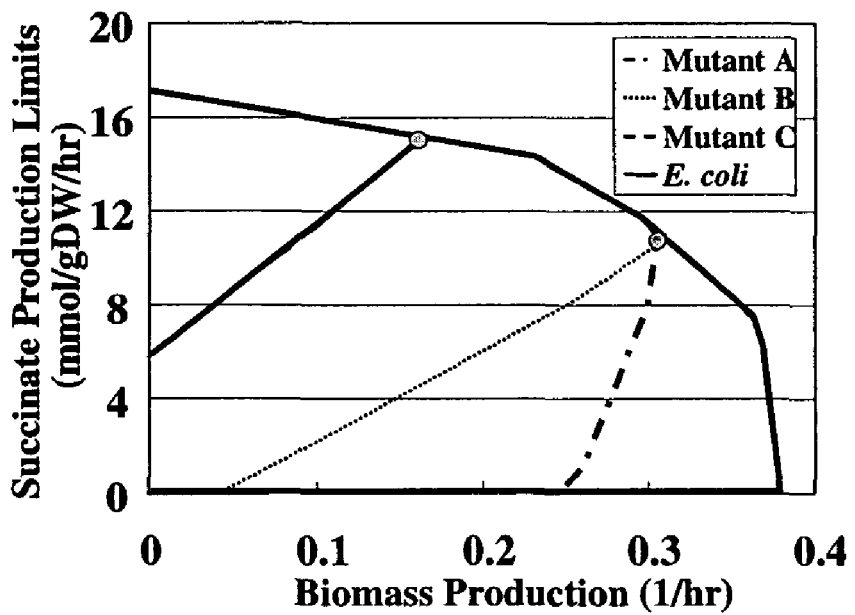
FIG. 3 shows (A) succinate or (B) lactate production limits under anaerobic conditions for mutant A (dash/dotted line), mutant B (dotted line), mutant C (short dashes) and the wild-type *E. coli* network (solid). The production limits are obtained by separately maximizing and minimizing succinate or lactate production for the biomass yields available to each network. The yellow points depict the solution identified by OptKnock (i.e., maximum chemical production at the maximum biomass yield).
Figure 3:
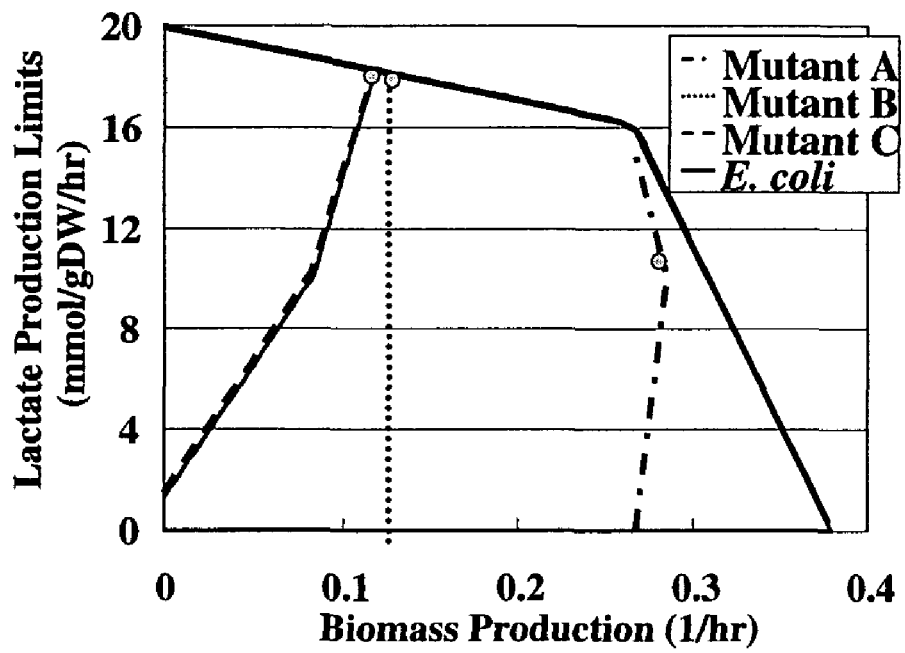

Table I summarizes three of the identified gene knockout strategies for succinate overproduction (i.e., mutants A, B, and C). The anaerobic flux distributions at the maximum biomass yields for the complete E. coli network (i.e., wild-type), mutant B, and mutant C are illustrated in FIGS. 2A-C. The results for mutant A suggested that the removal of two reactions (i.e., pyruvate formate lyase and lactate dehydrogenase) from the network results in succinate production reaching 63% of its theoretical maximum at the maximum biomass yield. This knockout strategy is identical to the one employed by Stols and Donnelly (Stols and Donnelly, 1997) in their succinate overproducing E. coli strain. Next, the envelope of allowable succinate versus biomass production was explored for the wild-type E. coli network and the three mutants listed in Table I. Note that the succinate production limits, shown in FIG. 3A, revealed that mutant A does not exhibit coupled succinate and biomass formation until the yield of biomass approaches 80% of the maximum. Mutant B, however, with the additional deletion of acetaldehyde dehydrogenase, resulted in a much earlier coupling of succinate with biomass yields.

A less intuitive strategy was identified for mutant C which focused on inactivating two PEP consuming reactions rather than eliminating competing byproduct (i.e., ethanol, formate, and lactate) production mechanisms. First, the phosphotransferase system was disabled requiring the network to rely exclusively on glucokinase for the uptake of glucose. Next, pyruvate kinase was removed leaving PEP carboxykinase as the only central metabolic reaction capable of draining the significant amount of PEP supplied by glycolysis. This strategy, assuming that the maximum biomass yield could be attained, resulted in a succinate yield approaching 88% of the theoretical maximum. In addition, FIG. 3A revealed significant succinate production for every attainable biomass yield, while the maximum theoretical yield of succinate is the same as that for the wild-type strain.

The OptKnock framework was next applied to identify knockout strategies for coupling lactate and biomass production. Table I shows three of the identified gene knockout strategies (i.e., mutants A, B, and C) and the flux distribution of mutant C at the maximum biomass yield is shown in FIG. 2D. Mutant A redirects flux toward lactate at the maximum biomass yield by blocking acetate and ethanol production. This result is consistent with previous work demonstrating that an adh, pta mutant E. coli strain could grow anaerobically on glucose by producing lactate (Gupta and Clark, 1989). Mutant B provides an alternate strategy involving the removal of an initial glycolysis reaction along with the acetate production mechanism. This results in a lactate yield of 90% of its theoretical limit at the maximum biomass yield. The vertical red line for mutant B in FIG. 3B indicates that the network could avoid producing lactate while maximizing biomass formation. This is due to the fact that OptKnock does not explicitly account for the "worst-case" alternate solution. It should be appreciated that upon the additional elimination of the glucokinase and ethanol production mechanisms, mutant C exhibited a tighter coupling between lactate and biomass production.

TABLE I

Biomass and chemical yields for various gene knockout strategies identified by OptKnock. The reactions and corresponding enzymes for each knockout strategy are listed. The maximum biomass and corresponding chemical yields are provided on a basis of 10 mmol/hr glucose fed and 1 gDW of cells. The rightmost column provides the chemical yields for the same basis assuming a minimal redistribution of metabolic fluxes from the wild-type (undeleted) E. coli network (MOMA assumption). For the 1,3-propanediol case, glycerol secretion was disabled for both knockout strategies.

| | | | | max $v_{biomass}$ | | min $\Sigma(v_0 - v)^2$ |
|---|---|---|---|---|---|---|
| | | | Succinate | | | |
| ID | Knockouts | Enzyme | Biomass (1/hr) | Succinate (mmol/hr) | | Succinate (mmol/hr) |
| Wild | "Complete network" | | 0.38 | 0.12 | | 0 |
| A | 1 COA + PYR → ACCOA + FOR | Pyruvate formate lyase | 0.31 | 10.70 | | 1.65 |
| | 2 NADH + PYR ↔ LAC + NAD | Lactate dehydrogenase | | | | |
| B | 1 COA + PYR → ACCOA + FOR | Pyruvate formate lyase | 0.31 | 10.70 | | 4.79 |
| | 2 NADH + PYR ↔ LAC + NAD | Lactate dehydrogenase | | | | |
| | 3 ACCOA + 2 NADH ↔ COA + ETH + 2 NAD | Acetaldehyde dehydrogenase | | | | |
| C | 1 ADP + PEP → ATP + PYR | Pyruvate kinase | 0.16 | 15.15 | | 6.21 |
| | 2 ACTP + ADP ↔ AC + ATP or | Acetate kinase | | | | |
| | ACCOA + Pi ↔ ACTP + COA | Phosphotransacetylase | | | | |
| | 3 GLC + PEP → G6P + PYR | Phosphotransferase system | | | | |
| | | | Lactate | | | |
| | | | max $v_{biomass}$ | | | min $\Sigma(v_0 - v)^2$ |
| ID | Knockouts | Enzyme | Biomass (1/hr) | Lactate (mmol/hr) | | Lactate (mmol/hr) |
| Wild | "Complete network" | | 0.38 | 0 | | 0 |
| A | 1 ACTP + ADP ↔ AC + ATP or | Acetate kinase | 0.28 | 10.46 | | 5.58 |

TABLE I-continued

Biomass and chemical yields for various gene knockout strategies identified by OptKnock. The reactions and corresponding enzymes for each knockout strategy are listed. The maximum biomass and corresponding chemical yields are provided on a basis of 10 mmol/hr glucose fed and 1 gDW of cells. The rightmost column provides the chemical yields for the same basis assuming a minimal redistribution of metabolic fluxes from the wild-type (undeleted) E. coli network (MOMA assumption). For the 1,3-propanediol case, glycerol secretion was disabled for both knockout strategies.

| ID | Knockouts | Enzyme | | | |
|----|-----------|--------|---|---|---|
| B | ACCOA + Pi ↔ ACTP + COA<br>2 ACCOA + 2 NADH ↔ COA + ETH + 2 NAD<br>1 ACTP + ADP ↔ AC + ATP or<br>ACCOA + Pi ↔ ACTP + COA<br>2 ATP + F6P → ADP + FDP or<br>FDP ↔ T3P1 + T3P2 | Phosphotransacetylase<br>Acetaldehyde dehydrogenase<br>Acetate kinase<br>Phosphotransacetylase<br>Phosphofructokinase<br>Fructose-1,6-bisphosphatate aldolase | 0.13 | 18.00 | 0.19 |
| C | 1 ACTP + ADP ↔ AC + ATP or<br>ACCOA + Pi ↔ ACTP + COA<br>2 ATP + F6P → ADP + FDP or<br>FDP ↔ T3P1 + T3P2<br>3 ACCOA + 2 NADH ↔ COA + ETH + 2 NAD<br>4 GLC + ATP → G6P + PEP | Acetate kinase<br>Phosphotransacetylase<br>Phosphofructokinase<br>Fructose-1,6-bisphosphatate aldolase<br>Acetaldehyde dehydrogenase<br>Glucokinase | 0.12 | 18.13 | 10.53 |

1,3-Propanediol

| | | | max $v_{biomass}$ | | min $\Sigma(v_0 - v)^2$ |
|---|---|---|---|---|---|
| ID | Knockouts | Enzyme | Biomass (1/hr) | 1,3-PD (mmol/hr) | 1,3-PD (mmol/hr) |
| Wild | "Complete network" | | 1.06 | 0 | 0 |
| A | 1 FDP → F6P + Pi or<br>FDP ↔ T3P1 + T3P2<br>2 13PDG + ADP ↔ 3PG + ATP or<br>NAD + Pi + T3P1 ↔ 13PDG + NADH<br>3 GL + NAD ↔ GLAL + NADH | Fructose-1,6-bisphosphatase<br>Fructose-1,6-bisphosphate aldolase<br>Phosphoglycerate kinase<br>Glyceraldehyde-3-phosphate dehydrogenase<br>Aldehyde dehydrogenase | 0.21 | 9.66 | 8.66 |
| B | 1 T3P1 ↔ T3P2<br>2 G6P + NADP ↔ D6PGL + NADPH or<br>D6PGL → D6PGC<br>3 DR5P → ACAL + T3P1<br>4 GL + NAD ↔ GLAL + NADH | Triosphosphate isomerase<br>Glucose 6-phosphate-1-dehydrogenase<br>6-Phosphogluconolactonase<br>Deoxyribose-phosphate aldolase<br>Aldehyde dehydrogenase | 0.29 | 9.67 | 9.54 |

Example 2

1,3-Propanediol (PDO) Production

In addition to devising optimum gene knockout strategies, OptKnock was used to design strains where gene additions were needed along with gene deletions such as in PDO production in E. coli. Although microbial 1,3-propanediol (PDO) production methods have been developed utilizing glycerol as the primary carbon source (Hartlep et al., 2002; Zhu et al., 2002), the production of 1,3-propanediol directly from glucose in a single microorganism has recently attracted considerable interest (Cameron et al., 1998; Biebl et al., 1999; Zeng and Biebl, 2002). Because wild-type E. coli lacks the pathway necessary for PDO production, the gene addition framework was first employed (Burgard and Maranas, 2001) to identify the additional reactions needed for producing PDO from glucose in E. coli. The gene addition framework identified a straightforward three-reaction pathway involving the conversion of glycerol-3-P to glycerol by glycerol phosphatase, followed by the conversion of glycerol to 1,3 propanediol by glycerol dehydratase and 1,3-propanediol oxidoreductase. These reactions were then added to the E. coli stoichiometric model and the OptKnock procedure was subsequently applied.

OptKnock revealed that there was neither a single nor a double deletion mutant with coupled PDO and biomass production. However, one triple and multiple quadruple knockout strategies that can couple PDO production with biomass production was identified. Two of these knockout strategies are shown in Table I. The results suggested that the removal of certain key functionalities from the E. coli network resulted in PDO overproducing mutants for growth on glucose. Specifically, Table I reveals that the removal of two glycolytic reactions along with an additional knockout preventing the degradation of glycerol yields a network capable of reaching 72% of the theoretical maximum yield of PDO at the maximum biomass yield. Note that the glyceraldehyde-3-phosphate dehydrogenase (gapA) knockout was used by DuPont in their PDO-overproducing E. coli strain (Nakamura, 2002). Mutant B revealed an alternative strategy, involving the removal of the triose phosphate isomerase (tpi) enzyme exhibiting a similar PDO yield and a 38% higher biomass yield. Interestingly, a yeast strain deficient in triose phosphate isomerase activity was recently reported to produce glycerol, a key precursor to PDO, at 80-90% of its maximum theoretical yield (Compagno et al., 1996).

Figure 4:
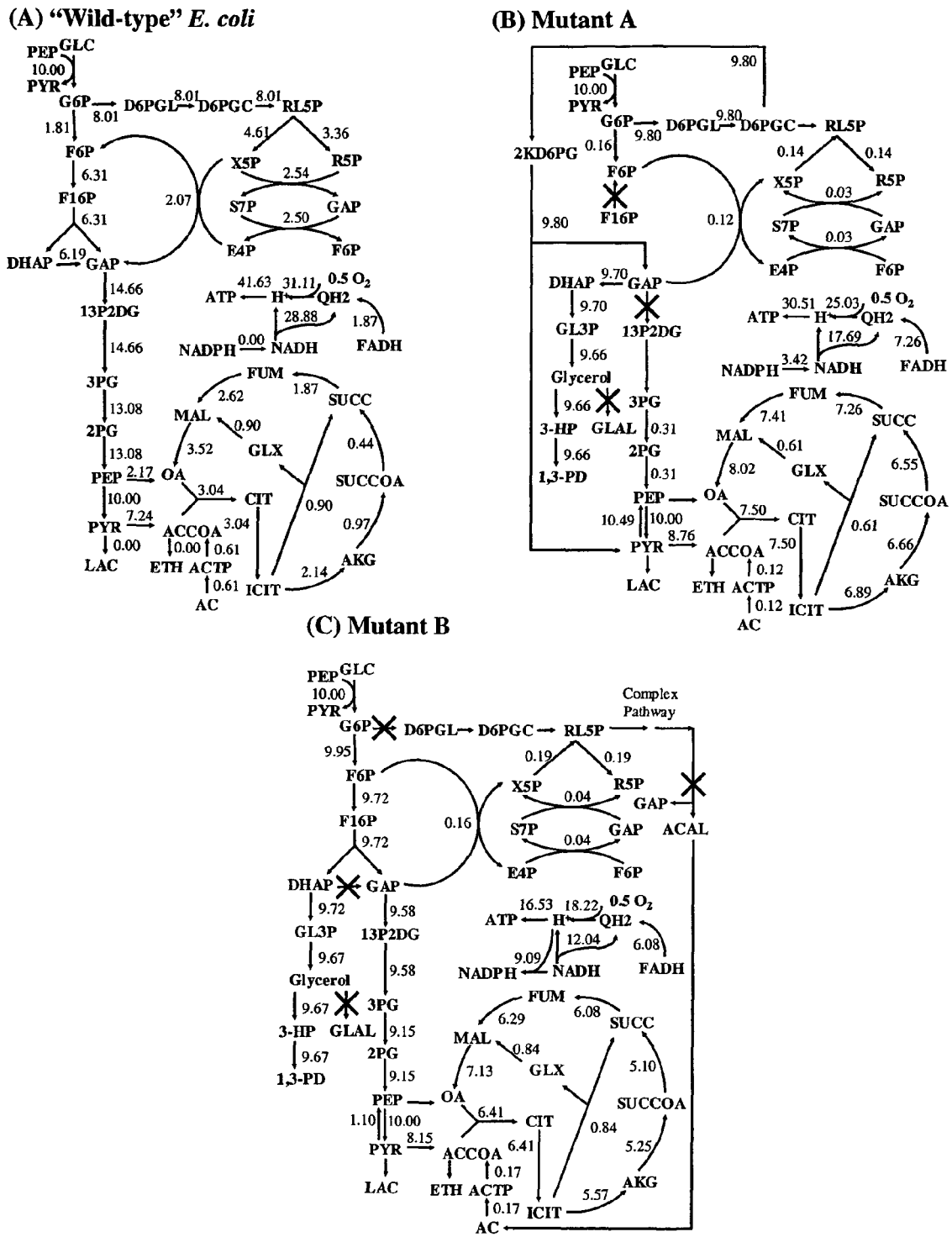
FIG. 4 shows the aerobic flux distributions of the (A) wild-type *E. coli*, (B) mutant A, and (C) mutant B networks that maximize biomass yield. Results for mutants A and B assume the reactions responsible for 1,3-propanediol production are available.

The flux distributions of the wild-type E. coli, mutant A, and mutant B networks that maximize the biomass yield are available in FIG. 4. Not surprisingly, further conversion of glycerol to glyceraldehyde was disrupted in both mutants A and B. For mutant A, the removal of two reactions from the top and bottom parts of glycolysis resulted in a nearly complete inactivation of the pentose phosphate and glycolysis (with the exception of triose phosphate isomerase) pathways. To compensate, the Entner-Doudoroff glycolysis pathway is activated to channel flux from glucose to pyruvate and glyceraldehyde-3-phosphate (GAP). GAP is then converted to glycerol which is subsequently converted to PDO. Energetic demands lost with the decrease in glycolytic fluxes from the wild-type E. coli network case, are now met by an increase in the TCA cycle fluxes. The knockouts suggested for mutant B redirect flux toward the production of PDO by a distinctly different mechanism. The removal of the initial pentose phosphate pathway reaction results in the complete flow of metabolic flux through the first steps of glycolysis. At the fructose bisphosphate aldolase junction, the flow is split into the two product metabolites: dihydroxyacetone-phosphate (DHAP) which is converted to PDO and GAP which continues through the second half of the glycolysis. The removal of the triosephosphate isomerase reaction prevents any interconversion between DHAP and GAP. Interestingly, a fourth knockout is predicted to retain the coupling between biomass formation and chemical production. This knockout prevents the "leaking" of flux through a complex pathway involving 15 reactions that together convert ribose-5-phosphate (R5P) to acetate and GAP, thereby decoupling growth from chemical production.

Figure 5:
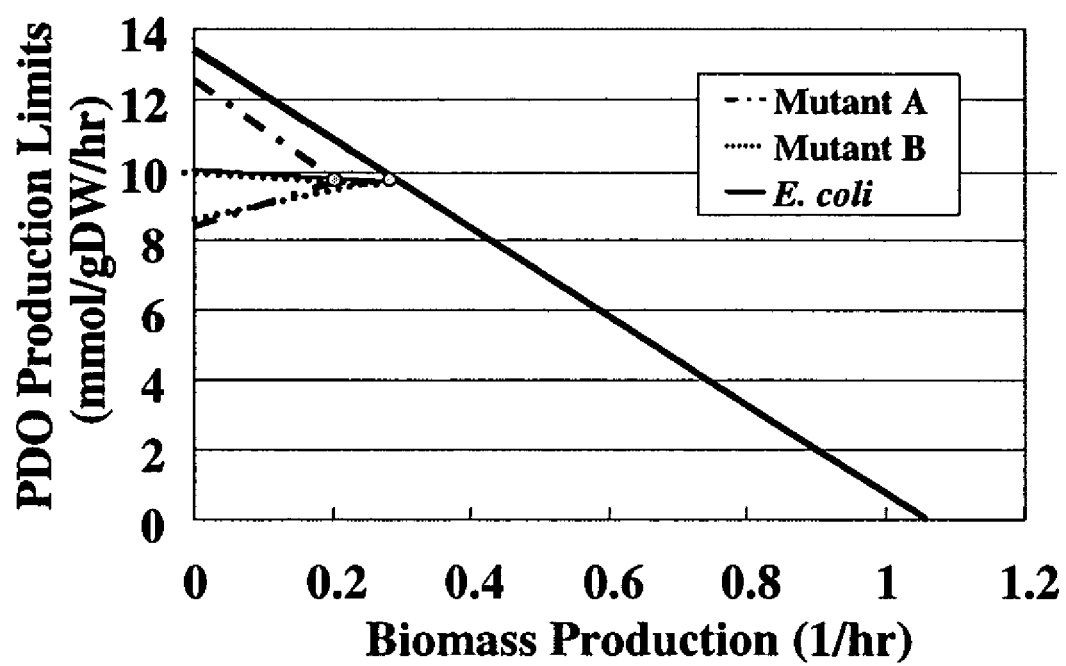
FIG. 5 shows 1,3-propanediol (PDO) production limits under aerobic conditions for mutant A (dash/dotted line), mutant B (dotted line), and the wild-type *E. coli* network (solid). The yellow points depict the solution identified by OptKnock (i.e., maximum chemical production at the maximum biomass yield).

Next, the envelope of allowable PDO production versus biomass yield is explored for the two mutants listed in Table I. The production limits of the mutants along with the original *E. coli* network, illustrated in FIG. 5, reveal that the wild-type *E. coli* network has no "incentive" to produce PDO if the biomass yield is to be maximized. On the other hand, both mutants A and B have to produce significant amounts of PDO if any amount of biomass is to be formed given the reduced functionalities of the network following the gene removals. Mutant A, by avoiding the tpi knockout that essentially sets the ratio of biomass to PDO production, is characterized by a higher maximum theoretical yield of PDO. The above described results hinge on the use of glycerol as a key intermediate to PDO. Next, the possibility of utilizing an alternative to the glycerol conversion route for 1,3-propandediol production was explored.

Applicants identified a pathway in *Chloroflexus aurantiacus* involving a two-step NADPH-dependant reduction of malonyl-CoA to generate 3-hydroxypropionic acid (3-HPA) (Menendez et al., 1999; Hugler et al., 2002). 3-HPA could then be subsequently converted chemically to 1,3 propanediol given that there is no biological functionality to achieve this transformation. This pathway offers a key advantage over PDO production through the glycerol route because its initial step (acetyl-CoA carboxylase) is a carbon fixing reaction. Accordingly, the maximum theoretical yield of 3-HPA (1.79 mmol/mmol glucose) is considerably higher than for PDO production through the glycerol conversion route (1.34 mmol/mmol glucose). The application of the OptKnock framework upon the addition of the 3-HPA production pathway revealed that many more knockouts are required before biomass formation is coupled with 3-HPA production. One of the most interesting strategies involves nine knockouts yielding 3-HPA production at 91% of its theoretical maximum at optimal growth. The first three knockouts were relatively straightforward as they involved removal of competing acetate, lactate, and ethanol production mechanisms. In addition, the Entner-Doudoroff pathway (either phosphogluconate dehydratase or 2-keto-3-deoxy-6-phosphogluconate aldolase), four respiration reactions (i.e., NADH dehydrogenase I, NADH dehydrogenase II, glycerol-3-phosphate dehydrogenase, and the succinate dehydrogenase complex), and an initial glycolyis step (i.e., phosphoglucose isomerase) are disrupted. This strategy resulted in a 3-HPA yield that, assuming the maximum biomass yield, is 69% higher than the previously identified mutants utilizing the glycerol conversion route.

Example 3

Alternative Cellular Objective

Minimization of Metabolic Adjustment

Figure 6:
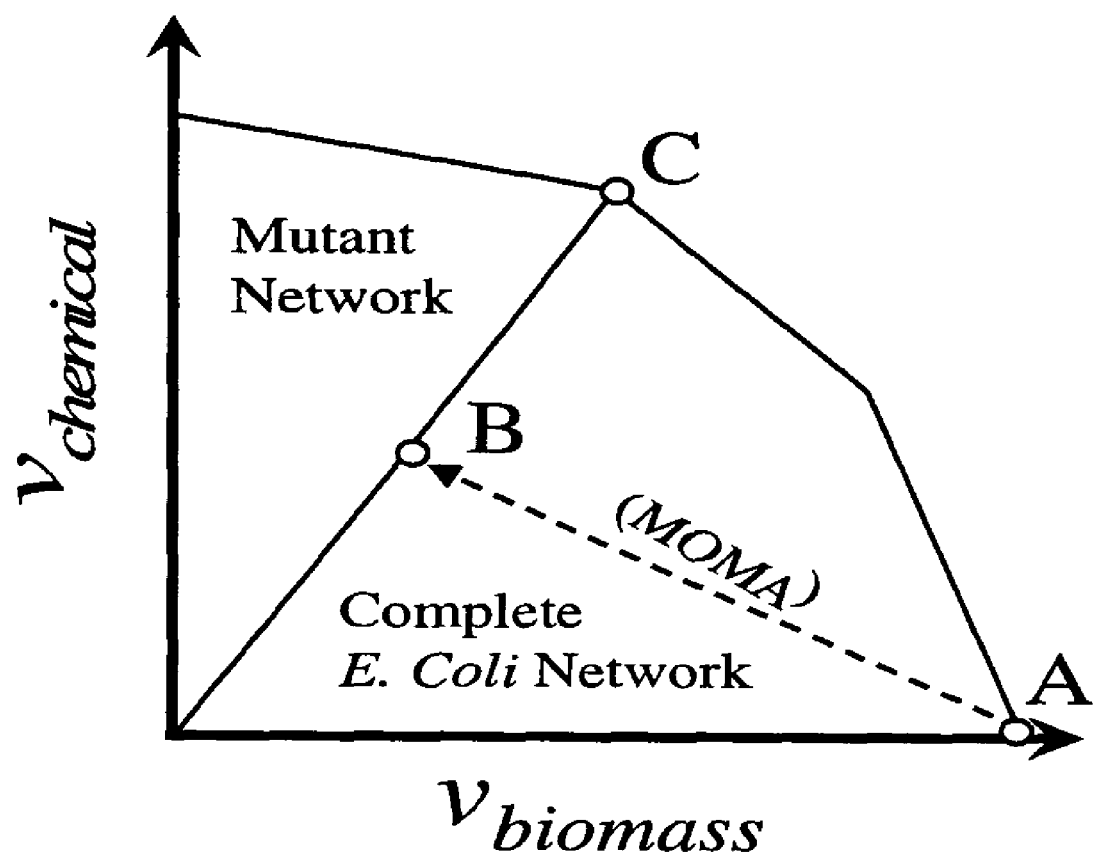
FIG. 6 shows projection of the multidimensional flux space onto two dimensions. The pink region represents flux ranges potentially reachable by both the mutant and complete networks, while the blue region corresponds to flux distributions rendered unreachable by the gene deletion(s). Point A represents the maximum biomass yield solution. Point B is the solution assuming the minimization of metabolic adjustment hypothesis for the mutant network, while point C is the solution assuming the mutant network will maximize its biomass yield.

All results described previously were obtained by invoking the maximization of biomass yield as the cellular objective that drives flux allocation. This hypothesis essentially assumes that the metabolic network could arbitrarily change and/or even rewire regulatory loops to maintain biomass yield maximality under changing environmental conditions (maximal response). Recent evidence suggests that this is sometimes achieved by the K-12 strain of *E. coli* after multiple cycles of growth selection (Ibarra et al., 2002). In this section, a contrasting hypothesis was examined (i.e., minimization of metabolic adjustment (MOMA) (Segre et al., 2002)) that assumed a myopic (minimal) response by the metabolic network upon gene deletions. Specifically, the MOMA hypothesis suggests that the metabolic network will attempt to remain as close as possible to the original steady state of the system rendered unreachable by the gene deletion(s). This hypothesis has been shown to provide a more accurate description of flux allocation immediately after a gene deletion event (Segre et al., 2002). FIG. 6 pictorially shows the two differing new steady states predicted by the two hypotheses, respectively. For this study, the MOMA objective was utilized to predict the flux distributions in the mutant strains identified by OptKnock. The base case for the lactate and succinate simulations was assumed to be maximum biomass formation under anaerobic conditions, while the base case for the PDO simulations was maximum biomass formation under aerobic conditions. The results are shown in the last column of Table 1. In all cases, the suggested multiple gene knock-out strategy suggests only slightly lower chemical production yields for the MOMA case compared to the maximum biomass hypothesis. This implies that the OptKnock results are fairly robust with respect to the choice of cellular objective.

The publications and other material used herein to illuminate the background of the invention or provide additional details respecting the practice, are herein incorporated by reference in their entirety.

The present invention contemplates numerous variations, including variations in organisms, variations in cellular objectives, variations in bioengineering objectives, variations in types of optimization problems formed and solutions used.

These and/or other variations, modifications or alterations may be made therein without departing from the spirit and the scope of the invention as set forth in the appended claims.

REFERENCES

Badarinarayana, V, Estep, P W, 3rd, Shendure, J, Edwards, J, Tavazoie, S, Lam, F, Church, G M. 2001. Selection analyses of insertional mutants using subgenic-resolution arrays. Nat Biotechnol 19(11): 1060-5.

Bard, J F. 1998. Practical bilevel optimization : algorithms and applications. Dordrecht ; Boston, Kluwer Academic.

Biebl, H, Menzel, K, Zeng, A P, Deckwer, W D. 1999. Microbial production of 1,3-propanediol. Appl Environ Microbiol 52: 289-297.

Burgard, A P, Maranas, C D. 2001. Probing the performance limits of the *Escherichia coli* metabolic network subject to gene additions or deletions. Biotechnol Bioeng 74: 364-375.

Burgard, A P, Maranas, C D. 2003. Optimization-based framework for inferring and testing hypothesized metabolic objective functions. Biotechnol Bioeng 82(6): 670-7.

Burgard, A P, Vaidyaraman, S, Maranas, C D. 2001. Minimal Reaction Sets for *Escherichia coli* Metabolism under Different Growth Requirements and Uptake Environments. Biotechnol Prog 17: 791-797.

Cameron, D C, Altaras, N E, Hoffman, M L, Shaw, A J. 1998. Metabolic engineering of propanediol pathways. Biotechnol Prog 14(1): 116-25.

Compagno, C, Boschi, F, Ranzi, B M. 1996. Glycerol production in a triose phosphate isomerase deficient mutant of *Saccharomyces cerevisiae*. Biotechnol Prog 12(5): 591-5.

Covert, M W, Palsson, B O. 2002. Transcriptional regulation in constraints-based metabolic models of *Escherichia coli*. J Biol Chem 277(31): 28058-64.

Covert, M W, Schilling, C H, Palsson, B O. 2001. Regulation of gene expression in flux balance models of metabolism. J Theor Biol 213(1): 73-88.

Datta, R, Tsai, S, Bonsignore, P, Moon, S, Frank, J R. 1995. Technological and economic potential of poly(lactic acid) and lactic acid derivatives. FEMS Microbiol. Rev. 16: 221-231.

Edwards, J S, Ibarra, R U, Palsson, B O. 2001. In silico predictions of *Escherichia coli* metabolic capabilities are consistent with experimental data. Nat Biotechnol 19(2): 125-30.

Edwards, J S, Palsson, B O. 2000. The *Escherichia coli* MG1655 in silico metabolic genotype: its definition, characteristics, and capabilities. Proc Natl Acad Sci USA 97(10): 5528-33.

Forster, J, Famili, I, Fu, P C, Palsson, B, Nielsen, J. 2003. Genome-scale reconstruction of the *Saccharomyces cerevisiae* metabolic network. Genome Research 13(2): 244-253.

Gupta, S, Clark, D P. 1989. *Escherichia coli* derivatives lacking both alcohol dehydrogenase and phosphotransacetylase grow anaerobically by lactate fermentation. J Bacteriol 171(7): 3650-5.

Hartlep, M, Hussmann, W, Prayitno, N, Meynial-Salles, I, Zeng, A P. 2002. Study of two-stage processes for the microbial production of 1,3-propanediol from glucose. Appl Microbiol Biotechnol 60(1-2): 60-6.

Hatzimanikatis, V, Emmerling, M, Sauer, U, Bailey, J E. 1998. Application of mathematical tools for metabolic design of microbial ethanol production. Biotechnol Bioeng 58(2-3): 154-61.

Heinrich, R, Rapoport, T A. 1974. A linear steady-state treatment of enzymatic chains. Eur. J. Biochem. 41: 89-95.

Hugler, M, Menendez, C, Schagger, H, Fuchs, G. 2002. Malonyl-coenzyme A reductase from *Chloroflexus aurantiacus*, a key enzyme of the 3-hydroxypropionate cycle for autotrophic CO(2) fixation. J Bacteriol 184(9): 2404-10.

Ibarra, R U, Edwards, J S, Palsson, B O. 2002. *Escherichia coli* K-12 undergoes adaptive evolution to achieve in silico predicted optimal growth. Nature 420(6912): 186-9.

Ignizio, J P, Cavalier, T M. 1994. Linear programming. Englewood Cliffs, N.J., Prentice Hall.

Kacser, H, Burns, J A. 1973. The control of flux. Symp. Soc. Exp. Biol. 27: 65-104.

Kompala, D S, Ramkrishna, D, Tsao, G T. 1984. Cybernetic Modeling of Microbial Growth on Multiple Substrates. Biotechnol Bioeng 26(11): 1272-1281.

Majewski, R A, Domach, M M. 1990. Simple constrained optimization view of acetate overflow in *Escherichia coli*. Biotechnol Bioeng 35: 732-738.

Menendez, C, Bauer, Z, Huber, H, Gad'on, N, Stetter, K O, Fuchs, G. 1999. Presence of acetyl coenzyme A (CoA) carboxylase and propionyl-CoA carboxylase in autotrophic Crenarchaeota and indication for operation of a 3-hydroxypropionate cycle in autotrophic carbon fixation. J Bacteriol 181(4): 1088-98.

Nakamura, C E. 2002. Production of 1,3-Propanediol by *E. coli*. presented at Metab Eng IV Conf: Tuscany, Italy.

Neidhardt, F C, Curtiss, R. 1996. *Escherichia coli* and *Salmonella*: cellular and molecular biology. Washington, D.C., ASM Press.

Papin, J A, Price, N D, Wiback, S J, Fell, D A, Palsson, B. 2003. Metabolic Pathways in the Post-Genome Era. Trends Biochem Sci, accepted.

Price, N D, Papin, J A, Schilling, C H, Palsson, B. 2003. Genome-scale Microbial In Silico Models: The Constraints-Based Approach. Trends Biotechnol, accepted.

Ramakrishna, R, Edwards, J S, McCulloch, A, Palsson, B O. 2001. Flux-balance analysis of mitochondrial energy metabolism: consequences of systemic stoichiometric constraints. Am J Physiol Regul Integr Comp Physiol 280 (3): R695-704.

Ramakrishna, R, Ramakrishna, D, Konopka, A E. 1996. Cybernetic Modeling of Growth in Mixed, Substitutable Substrate Environments: Preferential and Simultaneous Utilization. Biotechnol Bioeng 52: 141-151.

Schilling, C H, Covert, M W, Famili, I, Church, G M, Edwards, J S, Palsson, B O. 2002. Genome-scale metabolic model of *Helicobacter pylori* 26695. J Bacteriol 184(16): 4582-93.

Schilling, C H, Palsson, B O. 2000. Assessment of the metabolic capabilities of *Haemophilus influenzae* Rd through a genome-scale pathway analysis. J Theor Biol 203(3): 249-83.

Segre, D, Vitkup, D, Church, G M. 2002. Analysis of optimality in natural and perturbed metabolic networks. Proc Natl Acad Sci USA 99(23): 15112-7.

Stephanopoulos, G, Aristidou, A A, Nielsen, J. 1998. Metabolic engineering : principles and methodologies. San Diego, Academic Press.

Stols, L, Donnelly, M I. 1997. Production of succinic acid through overexpression of NAD(+)-dependent malic enzyme in an *Escherichia coli* mutant. Appl Environ Microbiol 63(7): 2695-701.

Varma, A, Boesch, B W, Palsson, B O. 1993. Stoichiometric interpretation of *Escherichia coli* glucose catabolism under various oxygenation rates. Appl Environ Microbiol 59(8): 2465-73.

Varma, A, Palsson, B O. 1993. Metabolic Capabilities of *Escherichia coli*: II. Optimal Growth Patterns. J. Theor. Biol. 165: 503-522.

Varma, A, Palsson, B O. 1994. Metabolic Flux Balancing: Basic Concepts, Scientific and Practical Use. Bio/Technology 12: 994-998.

Varner, J, Ramkrishna, D. 1999. Metabolic engineering from a cybernetic perspective. 1.
Theoretical preliminaries. Biotechnol Prog 15(3): 407-25.

Zeikus, J G, Jain, M K, Elankovan, P. 1999. Biotechnology of succinate acid production and markets for derived industrial products. Appl Microbiol Biotechnol 51: 545-552.

Zeng, A P, Biebl, H. 2002. Bulk chemicals from biotechnology: the case of 1,3-propanediol production and the new trends. Adv Biochem Eng Biotechnol 74: 239-59.

Zhu, M M, Lawman, P D, Cameron, D C. 2002. Improving 1,3-propanediol production from glycerol in a metaboli-

What is claimed is:

1. A method for determining candidates for gene deletions and additions using a model of a metabolic network associated with an organism, the method comprising:
   providing a model in a computer comprising an electronic representation of a plurality of metabolic reactions defining metabolite relationships;
   selecting at least one bioengineering objective function for the organism;
   selecting at least one cellular objective function for the organism;
   forming a linear optimization problem that couples the at least one cellular objective function with the at least one bioengineering objective function;
   executing commands in a suitably programmed computer for solving the linear optimization problem to provide an optimal solution for the bioengineering objective function that simultaneously requires optimality of the cellular objective function and yields at least one candidate gene deletion; and
   providing a visual output of the at least one candidate gene deletion to a user.

2. The method of claim 1 further comprising using the at least one candidate to genetically modify the organism.

3. The method of claim 1 wherein the bioengineering objective function is overproduction of a chemical.

4. The method of claim 1 wherein the bioengineering objective function is underproduction of a chemical.

5. The method of claim 1 wherein the cellular objective function is growth.

6. The method of claim 1 wherein the cellular objective is minimization of metabolic adjustment.

7. The method of claim 1 wherein the candidate is a candidate for gene deletion, and the optimization problem includes a binary value for specifying if reaction flux is active or inactive.

8. The method of claim 1 wherein the optimization problem is a bilevel optimization problem.

9. The method of claim 1 wherein the optimization problem is a mixed-integer optimization problem.

10. The method of claim 1 wherein the optimization problem includes at least one stoichiometric constraint.

11. The method of claim 1 wherein the optimization problem includes at least one chemical uptake constraint.

12. The method of claim 1 wherein the step of forming an optimization problem includes quantifying the cellular objective function as an aggregate reaction flux.

13. The method of claim 1 further comprising evaluating performance limits of the metabolic network with the at least one candidate based on ability of the network to meet the at least one cellular objective function.

14. The method of claim 1 wherein the cellular objective function is selected from the group consisting of: maximizing a growth rate, maximizing ATP production, minimizing metabolic adjustment, minimizing nutrient uptake, minimizing redox production, minimizing a Euclidean norm, and combinations thereof.

15. The method of claim 1 wherein the bioengineering objective is overproduction of glycerol and at least one candidate is for gene deletion and comprising genes coding for the enzymes fructose-1,6-bisphosphatase, fructose-1,6-bisphosphatase aldolase, phosphoglycerate kinase, glyceraldehydes-3-phosphate dehydrogenase, phosphoenolpyruvate synthase, NADH dehydrogenase I, phosphogluconate dehydratase, 2-keto-3-deoxy-6-phosphofluconate aldolase, triosphosphate isomerase, glucose 6-phosphate-1-dehydrogenase, 6-phosphogluconolactonase-, deoxyribose-phosphate aldolase, aldehyde dehydrogenase, or combinations thereof.

16. The method of claim 1 wherein the bioengineering objective is overproduction of 1,3-propanediol and at least one candidate is for gene deletion and comprising genes coding for the enzymes fructose-1,6-bisphosphatase, fructose-1,6-bisphosphatase aldolase, phosphoglycerate kinase, glyceraldehyde-3-phosphate dehydrogenase, triosphosphate isomerase, glucose 6-phosphate-1-dehydrogenase, 6-phosphogluconolactonase, deoxyribose-phosphate aldolase, aldehyde dehydrogenase, or combinations thereof.

17. The method of claim 1 wherein the bioengineering objective is overproduction of succinate and at least ape candidate is for gene deletion and comprising genes coding for the enzymes pyruvate formate lyase, acetaldehyde dehydrogenase, pyruvate kinase, FOF1-ATPase, NADH dehydrogenase I, fumarase, D-Lactate dehydrogenase, pyridine nucleotide transhydrogenase, phosphotransacetylase, acetate kinase, phosphotransferase, or combinations thereof.

18. The method of claim 1 wherein the bioengineering objective function is overproduction of lactate and at least one candidate is for gene deletion and comprising genes coding for the enzymes phosphotransacetylase, acetate kinase, phosphofructokinase, fructose-4 1,6-bisphosphatase aldolase, triosphosphate isomerase, acetaldehyde dehydrogenase, glucokinase, or combinations thereof.

19. A computer-based method for determining candidates for gene deletions using a model of a metabolic network associated with an organism, the method comprising:
   providing a model in a computer comprising an electronic representation of a plurality of metabolic reactions defining metabolite relationships;
   inputting at least one bioengineering objective function;
   receiving as input as least one cellular objective function;
   forming a linear optimization problem that quantities the at least one cellular objective function as an aggregate reaction flux and couples the at least one cellular objective function with the at least one bioengineering objective function;
   executing commands in a suitably programmed computer for solving the linear optimization problem to provide an optimal solution for the bioengineering objective function that simultaneously requires optimality of the cellular objective function and yields at least one candidate gene deletion; and
   visually outputting the at least one candidate gene deletion to a user.

20. The method of claim 1 wherein the cellular objective function comprises maximizing a growth rate.

21. The method of claim 1, further comprising solving the linear optimization problem to yield at least one candidate gene addition.

22. The computer-based method of claim 19, further comprising solving the linear optimization problem to yield at least one candidate gene addition.

* * * * *

UNITED STATES PATENT AND TRADEMARK OFFICE
CERTIFICATE OF CORRECTION

PATENT NO. : 8,027,821 B2  Page 1 of 1
APPLICATION NO. : 10/616659
DATED : September 27, 2011
INVENTOR(S) : Costas D. Maranas et al.

It is certified that error appears in the above-identified patent and that said Letters Patent is hereby corrected as shown below:

Column 1, line 7, after "DE-FG03-01ER25499" delete "." and insert --,--.

Column 18, Claim 19, line 41, after "problem that" "quantities" should read --quantifies--.

Signed and Sealed this
Eighth Day of November, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,027,821 B2 | Page 1 of 1 |
| APPLICATION NO. | : 10/616659 | |
| DATED | : September 27, 2011 | |
| INVENTOR(S) | : Maranas et al. | |

It is certified that error appears in the above-identified patent and that said Letters Patent is hereby corrected as shown below:

Col. 18, Claim 17, Line 19:
after "least" delete "ape" and insert --one--

Col. 18, Claim 19, Line 40:
after "input" delete "as" and insert --at--

Signed and Sealed this
Third Day of January, 2012

David J. Kappos
*Director of the United States Patent and Trademark Office*

UNITED STATES PATENT AND TRADEMARK OFFICE
CERTIFICATE OF CORRECTION

PATENT NO. : 8,027,821 B2
APPLICATION NO. : 10/616659
DATED : September 27, 2011
INVENTOR(S) : Maranas et al.

It is certified that error appears in the above-identified patent and that said Letters Patent is hereby corrected as shown below:

Col. 18, Claim 16, Lines 12-13:
DELETE after fructose-1,6-bisphosphatase, "fructose-1,6-bisphosphatase aldolase,"
ADD after fructose-1,6-bisphosphatase, --fructose-1,6-bisphate aldolase,--

Col. 18, Claim 18, line 30:
DELETE after fructose-4 "1,6-bisphosphatase aldolase,"
ADD after fructose-4 --1,6-bisphosphate aldolase,--

Signed and Sealed this
Thirty-first Day of January, 2012

David J. Kappos
*Director of the United States Patent and Trademark Office*